US011227162B1

(12) United States Patent
Lu et al.

(10) Patent No.: US 11,227,162 B1
(45) Date of Patent: Jan. 18, 2022

(54) MULTILAYER INFORMATION DYNAMICS FOR ACTIVITY AND BEHAVIOR DETECTION

(71) Applicant: HRL Laboratories, LLC, Malibu, CA (US)

(72) Inventors: Tsai-Ching Lu, Thousand Oaks, CA (US); Kang-Yu Ni, Calabasas, CA (US); Ryan M. Uhlenbrock, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 1287 days.

(21) Appl. No.: 15/497,202

(22) Filed: Apr. 25, 2017

Related U.S. Application Data

(60) Provisional application No. 62/376,220, filed on Aug. 17, 2016.

(51) Int. Cl.
| | | |
|---|---|---|
| *G06K 9/00* | (2006.01) | |
| *G06K 9/62* | (2006.01) | |
| *G06N 20/00* | (2019.01) | |
| *G08B 13/196* | (2006.01) | |
| *A61B 5/103* | (2006.01) | |
| *G06F 15/00* | (2006.01) | |

(Continued)

(52) U.S. Cl.
CPC .......... *G06K 9/00771* (2013.01); *G06K 9/62* (2013.01); *G06K 9/6292* (2013.01); *G06N 20/00* (2019.01); *A61B 5/103* (2013.01); *G06F 15/00* (2013.01); *G06Q 30/02* (2013.01); *G06Q 99/00* (2013.01); *G08B 13/19615* (2013.01)

(58) Field of Classification Search
CPC .... G06K 9/00771; G06K 9/62; G06K 9/6292; G06N 20/00; G06F 15/00; G06Q 30/02; G06Q 99/00; G08B 13/19615; A61B 5/103
USPC ........................................................... 706/12
See application file for complete search history.

(56) References Cited

U.S. PATENT DOCUMENTS

| | | | | |
|---|---|---|---|---|
| 5,846,189 A | * | 12/1998 | Pincus ................... | G16H 40/63 600/301 |
| 7,013,451 B1 | * | 3/2006 | Teig ...................... | G06F 30/394 716/129 |

(Continued)

OTHER PUBLICATIONS

Chikhaoui et al., "Discovering and Tracking Influencer-Influencee Relationships Between Online Communities", 2015 International Conference on Data Science and Advanced Analysis (DSAA), Oct. 19-21, 2015 (Year: 2015).*

(Continued)

*Primary Examiner* — Tsu-Chang Lee
(74) *Attorney, Agent, or Firm* — Tope-McKay & Associates

(57) ABSTRACT

Described is a system for activity and behavior detection in a target system. Raw data extracted from various heterogeneous sources of the target system is fused across spatial and temporal scales into a multi-graph representation. Information flows of the multi-graph representation are analyzed using a set of multi-layer information dynamic measures. Based on the set of multi-layer information dynamic measures, at least one of an economic and social indicator of emerging activity of interest in the target system is derived. The indicator is then used for prediction of future activity of interest in the target system.

27 Claims, 15 Drawing Sheets

(51) Int. Cl.
  *G06Q 99/00* (2006.01)
  *G06Q 30/02* (2012.01)

(56) References Cited

U.S. PATENT DOCUMENTS

2016/0106339 A1* 4/2016 Behzadi ............... A61B 5/7275
                                                    600/302
2018/0233014 A1* 8/2018 Wilkinson ......... G08B 21/0484

OTHER PUBLICATIONS

Proceedings of the Nineteen Conference on Uncertainty in Artificial Intelligence, UAI2003 (Year: 2003).*

N-K. Ni and T-C. Lu, Information Dynamic Spectrum Characterizes System Instability toward Critical Transitions, EPJ Data Science, 3: p. 28, 2014.

J. Borge-Holthefer, N. Perra, B. Goncalves, S. Gonzalez-Bailon, A. Arenas, Y. Moreno, and A. Vespignani. The dynamics of information-driven coordination phenomena: A transfer entropy analysis, Science Advance, 2:5, e1501158, 2016, pp. 1-8.

C. E. Shannon, "A Mathematical Theory of Communication". Bell System Technical Journal 27 (3): pp. 379-423, 1948.

Batty, Michael, et al. "Entropy, complexity, and spatial information." Journal of geographical systems 16.4 (2014) pp. 363-385.

T. Schreiber, "Measuring information transfer," Phys Rev Lett, 2000, 85(2): pp. 461-464.

* cited by examiner

| | |
|---|---|
| Data | AIS data and ship-to-ship, ship-to-shore, ship-to-central office sensor and communication data |
| Network | • Node: {Vessel/Office/Shore, Sensor}<br>• Static Edge: Frequency of a vessel registered by a sensor<br>• Temporal Edge: Time stamp, sampling, duration of a vessel registered by a sensor<br>• Spatial Tag: Associated with node entity |
| Exploratory Analysis | • Individual vessel trajectory analysis: Characterize individual vessel (class of similar vessels,…) to establish normal behavior characteristics by applying network metrics (e.g. centrality, clusters, ..) and extract individual behavior motifs of vessel movements to detect anomalies of tampering AIS, outlier routes, access to unauthorized zones, etc.<br>• Fleet vessel trajectory analysis: Establish fleet movement and communication patterns by network metrics at modularity level with group behavior motifs to detect anomalies in their sequence of actions (e.g. smuggling of fisheries) or collective actions (coordinated movement). |

FIG. 5

| Data | Port log data, National Oceanic Atmospheric Administration (NOAA), Food and Agriculture Organization (FAO) data, port-authority data |
|---|---|
| Network | • Node: {Vessel, Truck, Factory, Retails}<br>• Static Edge: Frequency (amount) of good transports<br>• Temporal Edge: Time stamp/sampling/duration of good transfers between nodes<br>• Spatial Tag: Associated with node entity |
| Exploratory Analysis | • Fishery traceability analysis: Characterize fishery product flows to establish normal behavior characteristics of fisheries transfer to perform network analysis for the detection of smuggling/mixing illegal fishers into legal fisheries, and the identification of potential points of smuggling activities<br>• Vessel support logistics analysis: : Characterize vessel supports (fuel, shipping) to establish normal behavior of vessel support activities for the detection and extraction of unauthorized (unconventional) vessel logistics supports |

FIG. 6

| Data | Twitter, Tumblr, Craig List, Forum, Yelp, cell phone data |
|---|---|
| Network | • Node: {Individual, group, organization}<br>• Static Edge: Frequency of mention of fishery product or fisheries activities, and normal communications<br>• Temporal Edge: Time stamp, sampling, duration of communications<br>• Spatial Tag: Associated with node entity |
| Exploratory Analysis | • Communication behavior pattern analysis: Characterize communication patterns by extracting metrics (e.g. centrality, clusters, ..) and behavior motifs to detect anomalies in communication patterns.<br>• Emerging topic analysis: Characterize baseline fishery consumption, restaurant evaluation, communication pattern trends to detect early activity shift related to illegal fishing |

FIG. 7

|  | Communication | | | Movement | | | Fishery | | |
|---|---|---|---|---|---|---|---|---|---|
|  | $z_1$ $z_2$ | ... | $z_n$ | $z_1$ $z_2$ | ... | $z_n$ | $z_1$ $z_2$ | ... | $z_n$ |
| Communication $z_1$ $z_2$ ... $z_n$ | Weighted (temporal) communication frequency between zones (observable) $M_{CC}(t)$ | | | Weighted (temporal) coordinated ship movements per communication flow frequency between zones (inferred) $M_{CV}(t)$ | | | Weighted (temporal) coordinated fisheries transport per communication flow frequency between zones (inferred) $M_{CF}(t)$ | | |
| Movement $z_1$ $z_2$ ... $z_n$ | Weighted (temporal) coordinated communications per ship movement flows between zones (inferred) $M_{VC}(t)$ | | | Weighted (temporal) frequency of directional ship movements between zones (observable) $M_{VV}(t)$ | | | Weighted (temporal) coordinated fisheries transport per ship movements between zones (inferred) $M_{VF}(t)$ | | |
| Fishery $z_1$ $z_2$ ... $z_n$ | Weighted (temporal) coordinated communications per fisheries transport between zones (inferred) $M_{FC}(t)$ | | | Weighted (temporal) coordinated ship movements per fisheries transports between zones (inferred) $M_{FV}(t)$ | | | Weighted (temporal) frequency of directional fisheries transport between zones (observable) $M_{FF}(t)$ | | |

FIG. 11

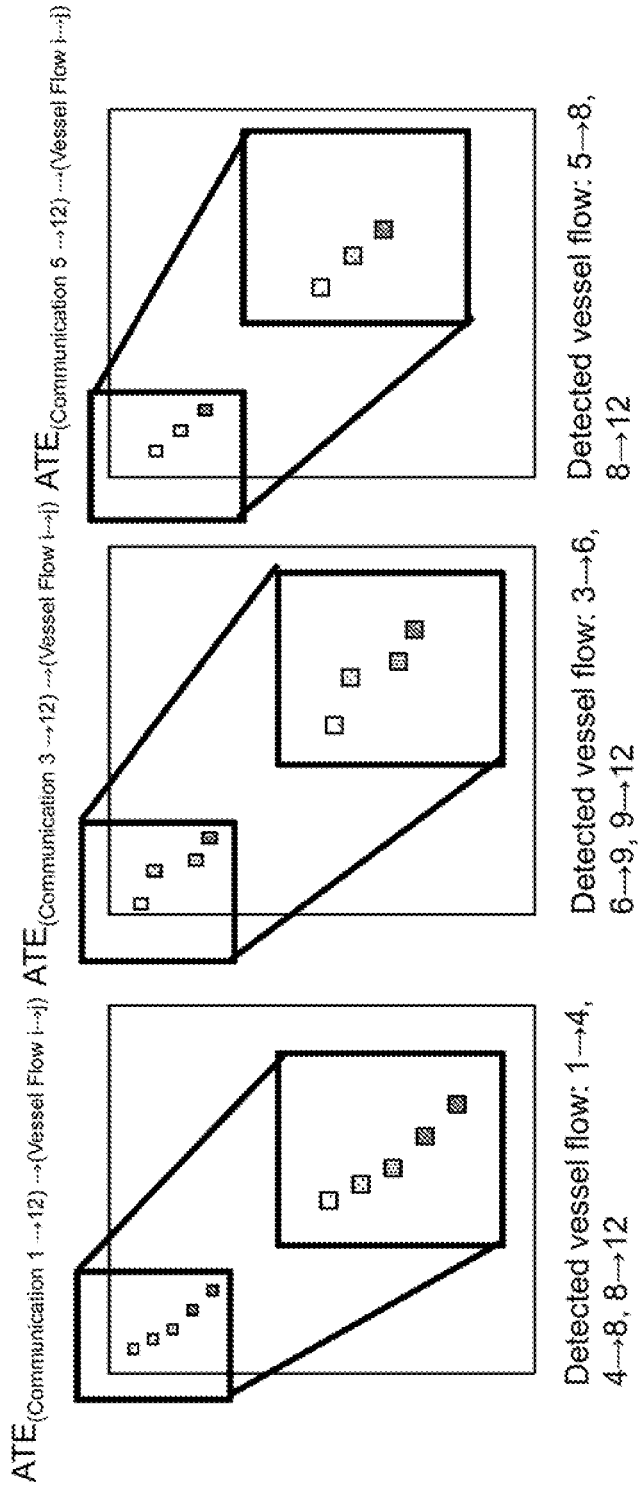

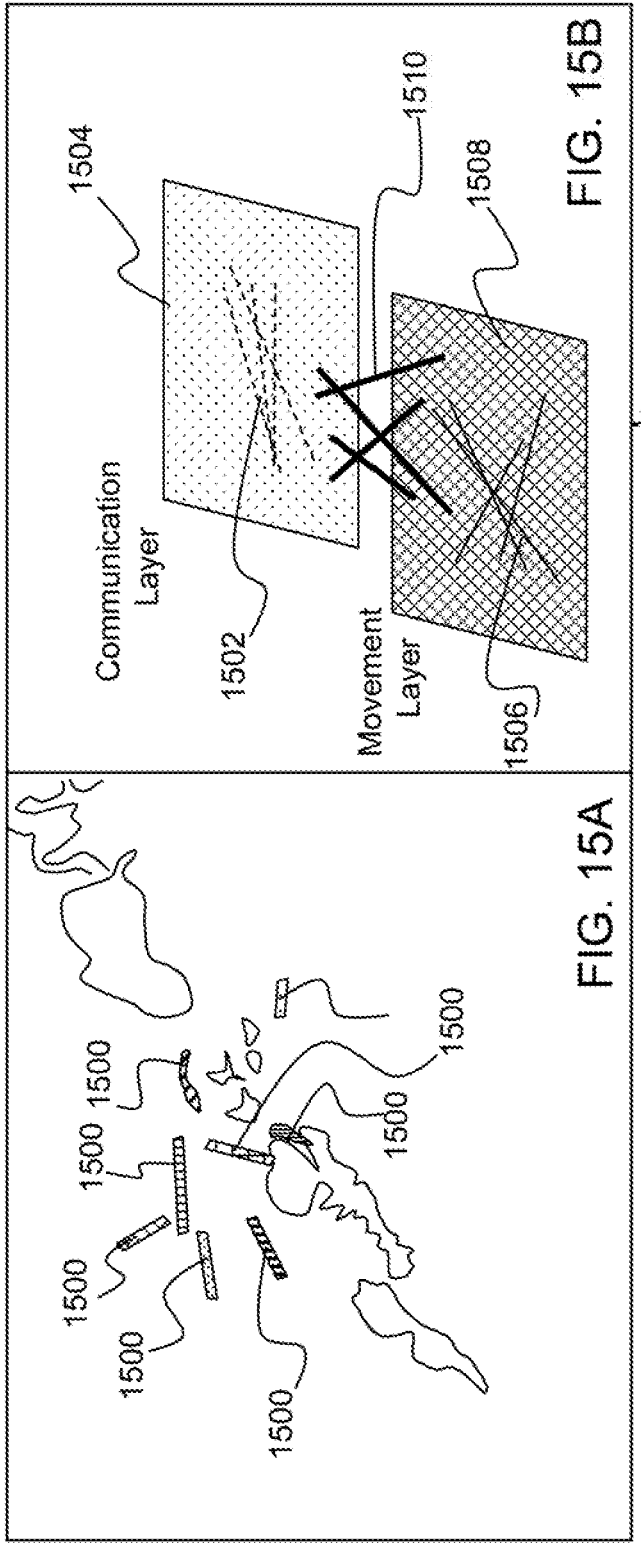
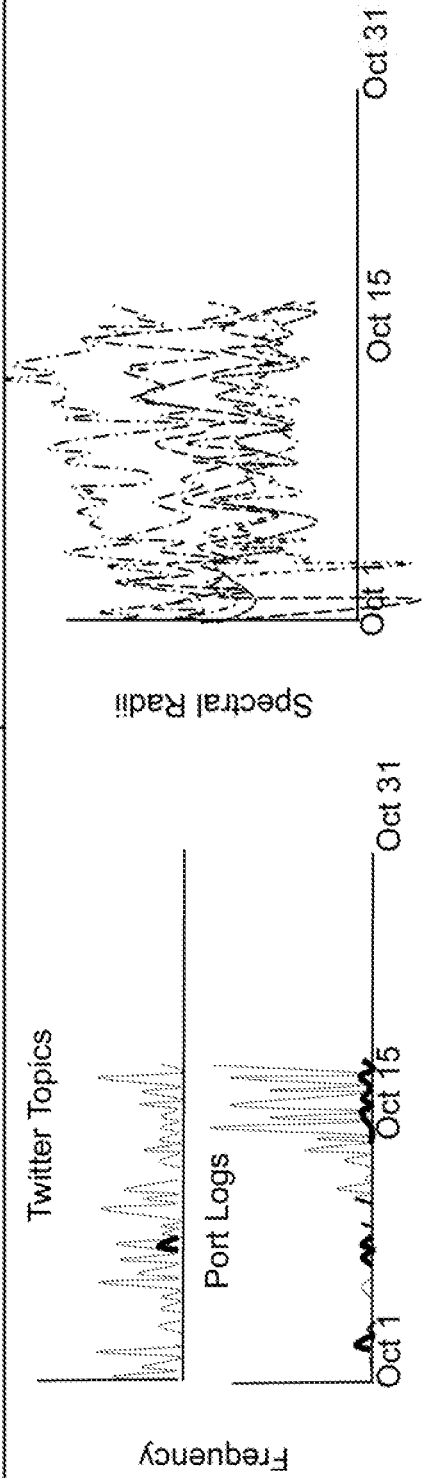
FIG. 15A
FIG. 15B
FIG. 15C
FIG. 15D

MULTILAYER INFORMATION DYNAMICS FOR ACTIVITY AND BEHAVIOR DETECTION

STATEMENT REGARDING FEDERALLY SPONSORED RESEARCH OR DEVELOPMENT

This invention was made with government support under U.S. Government Contract Number WCF7 PC 1141899 NRO NEBU MIDWAY. The government has certain rights in the invention.

CROSS-REFERENCE TO RELATED APPLICATIONS

This is a Non-Provisional application of U.S. Provisional Patent Application No. 62/376,220, filed Aug. 17, 2016, entitled, "Multilayer Information Dynamics for Activity and Behavior Detection", the entirety of which is incorporated herein by reference.

BACKGROUND OF INVENTION

(1) Field of Invention

The present invention relates to a system for activity and behavior detection in a target system and, more particularly, to a system for activity and behavior detection in a target system using multi-graph modeling.

(2) Description of Related Art

Information theory is the study of the quantification, storage, and communication of information. Prior work in the area of information-theoretic measure includes Shannon entropy (described in C. E. Shannon, A Mathematical Theory of Communication," Bell System Technical Journal 27 (3): 379-423, 1948), spatial entropy (described in Batty, Michael, et al. "Entropy, complexity, and spatial information," Journal of geographical systems 16.4 (2014): 363-385), and transfer entropy (described in T. Schreiber, "Measuring information transfer," Phys Rev Lett 2000, 85(2): 461-464), all of which are hereby incorporated by reference as though fully set forth herein.

Prior work has described using directional information transfer, such as associative transfer entropy (described in N-K, Ni and T-C, Lu, "Information Dynamic Spectrum Characterizes System Instability toward Critical Transitions," EPJ Data Science, 3:28, 2014, which is hereby incorporated by reference as though fully set forth herein), and derived measures (described in Borge-Holthefer, N. Perra, B. Goncalves, S. Gonzalez-Bailon, A. Arenas, Y. Moreno, and A. Vespignani, "The dynamics of information-driven coordination phenomena: A transfer entropy analysis," Science Advance, 2:5, e1501158, 2016, which is hereby incorporated by reference as though fully set forth herein), to detect and predict emerging phenomena in complex systems. However, both Ni and Borge-Heather consider only single data sources, and Ni only considers information dynamics in a single layer. Because such prior art techniques only consider single sources or operate in a single layer of a network, they are unable to fuse information from multiple sources and operate through multi-layer networks.

Thus, a continuing need exists for a system that can fuse information from multiple heterogeneous data sources into multi-layer information dynamic networks.

SUMMARY OF INVENTION

The present invention relates to a system for activity and behavior detection in a target system and, more particularly, to a system for activity and behavior detection in a target system using multi-graph modeling. The system comprises one or more processors and a non-transitory computer-readable medium having executable instructions encoded thereon such that when executed, the one or more processors perform multiple operations. Raw data extracted from various heterogeneous sources of the target system are fused across spatial and temporal scales into a multi-graph representation. Information flows of the multi-graph representation are analyzed using a set of multi-layer information dynamic measures. Based on the set of multi-layer information dynamic measures, at least one of an economic and a social indicator of emerging activity of interest in the target system is derived. The at least one of the economic and social indicator is then used for prediction of activity of interest in the target system.

In another aspect, values are determined for a supra-Laplacian matrix as an indicator for monitoring emerging instability and changes in dependency in the target system.

In another aspect, a responsive action is initiated in response to the prediction of the at least one future behavior and/or activity of interest in the target system.

In another aspect, the set of multi-layer information dynamic measures comprises a flow entropy measure that quantifies flow complexity, and a flow transfer entropy measure that determines flow transfer dynamics on the multi-graph representation.

In another aspect, the set of multi-layer information dynamic measures comprises a flow supra-Laplacian matrix measure that captures inter-layer and intra-layer flow dependency.

In another aspect, the system resamples, interpolates, and aligns raw data extracted from heterogeneous database sources into spatially aligned time series of the multi-graph representation.

In another aspect, a fishing activity system is modeled with the multi-graph representation. The multi-graph representation comprises a maritime activity network layer for modeling movement and communication patterns observed from heterogeneous sensor data sources, a supply-chain network layer for modeling logistics of fishing activities, and a social network layer for modeling social communication of employees related to fishing.

In another aspect, the multi-graph representation comprises a plurality of layers, and wherein inter-layer and intra-layer dependencies of the multi-graph representation are determined using an associative transfer entropy (ATE) measure.

In another aspect, an ATE measure is determined between all pairs of time series within and between layers of the multi-graph representation, resulting in a plurality of ATE measures. The plurality of ATE measures are arranged into a plurality of ATE matrices. A spectral radius is calculated on each ATE matrix, resulting in a spectral radius time series. The spectral radius time series is used to detect a transition in behavior and/or activity in the target system.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 5 is a table illustrating that maritime activity network modeling can support exploratory data analysis according to some embodiments of the present disclosure;

FIG. 6 is a table illustrating that supply-chain network modeling can support exploratory data analysis according to some embodiments according to some embodiments of the present disclosure;

FIG. 7 is a table illustrating that social network modeling of agents involved in fisheries activity can support identification of early indicators for emerging or changing behaviors in illegal fishing according to some embodiments of the present disclosure;

FIG. 11 is an illustration of a flow supra adjacency matrix defined to capture maritime activity dependency according to some embodiments of the present disclosure;

FIG. 13A is an illustration of a detected vessel flow path corresponding to the expected ground truth vessel flows given communication patterns according to some embodiments of the present disclosure;

FIG. 13B is a plot illustrating inferred associative transfer entropy (ATE) between communication flow 1→12 and vessel flow i→j according to some embodiments of the present disclosure;

FIG. 13C is a plot illustrating inferred ATE between communication flow 3→12 and vessel flow i→j according to some embodiments of the present disclosure;

FIG. 13D is a plot illustrating inferred ATE between communication flow 5→12 and vessel flow i→j according to some embodiments of the present disclosure;

FIG. 15A illustrates automatic identification system (AIS) tracks according to some embodiments of the present disclosure;

FIG. 15B illustrates inferred multi-layer network with communication flows, movement flows, and their dependency changing over time according to some embodiments of the present disclosure;

FIG. 15C illustrates time series of Twitter country-fishery co-mentions and port log time series according to some embodiments of the present disclosure; and FIG. 15D illustrates the ATE spectral radius of inferred maritime activities according to some embodiments of the present disclosure.

DETAILED DESCRIPTION

Figure 1:
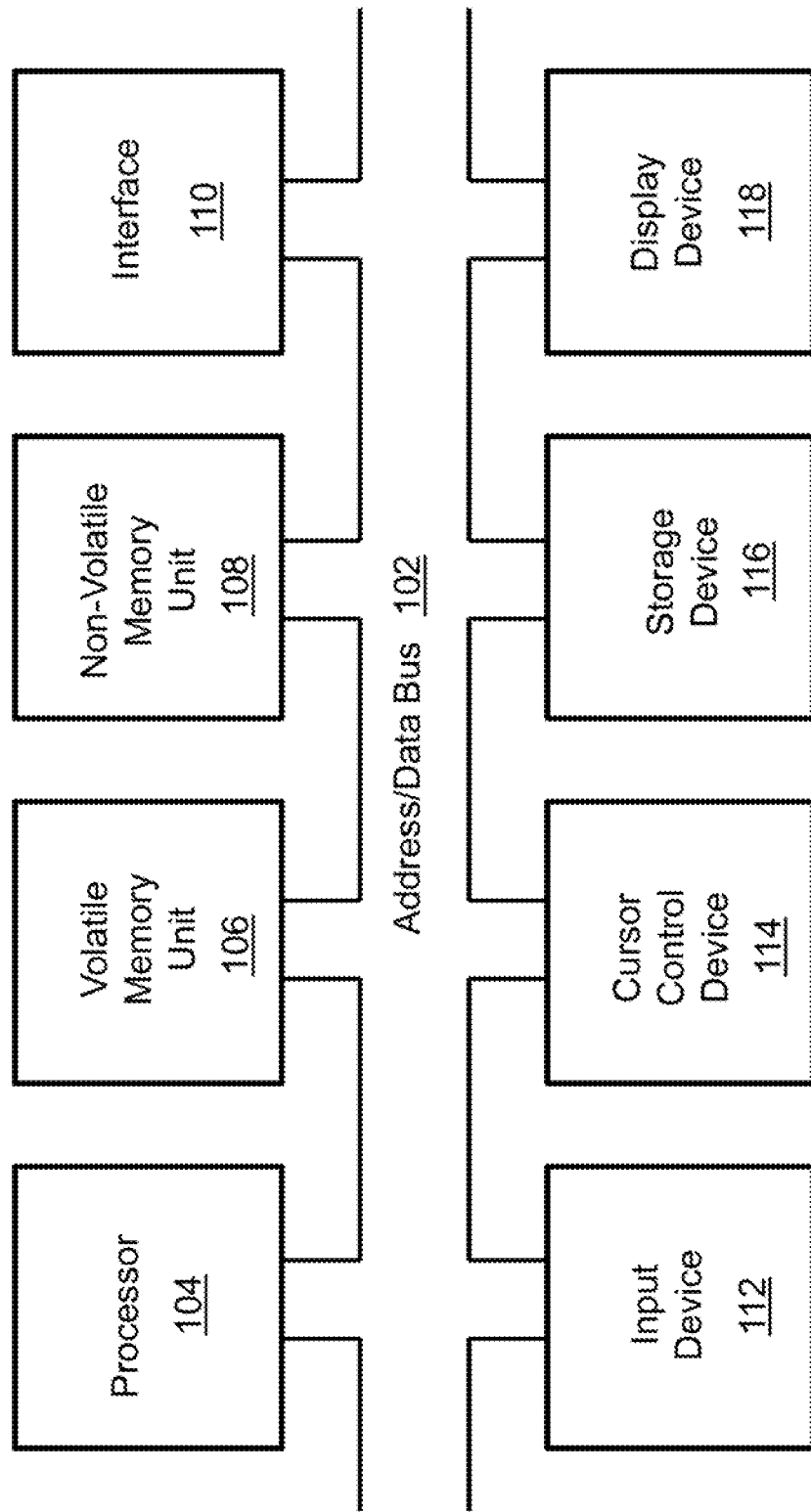
FIG. 1 is a block diagram depicting the components of a system for behavior detection according to some embodiments of the present disclosure.

The present invention relates to a system for activity and behavior detection in a target system and, more particularly, to a system for activity and behavior detection in a target system using multi-graph modeling.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

(2) Principal Aspects

Various embodiments of the invention include three "principal" aspects. The first is a system for behavior detection. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
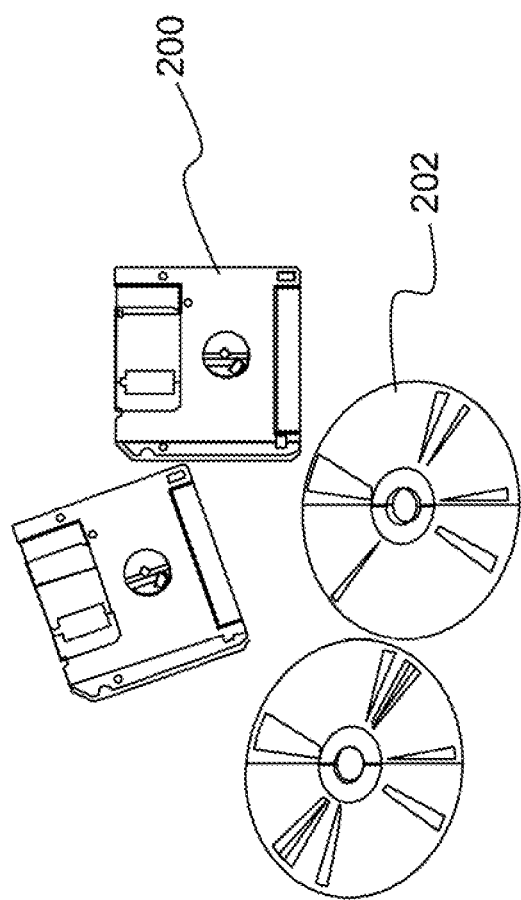
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Described is a unique multi-layer information dynamics framework and computational methods to monitor, detect, and infer emerging activities and behaviors, such as "coordinated movements" and "silence before actions", in a target system (e.g., illegal fishing, etc.). It should be understood that the system of this disclosure can be used to monitor, detect, and infer activities and behaviors in a variety of systems. While the use of illegal fishing is used for illustrative purposes, the invention is not intended to be limited thereto. For example, with respect to the target system of fishing, "coordinated movements" refers to the coordination of fleets of vessels, where each vessel is given a specific task. For instance, one vessel might coordinate fleet movements to patrol in an area where fishing is not allowed. Another vessel might be designated to direct fleet dispersal in the event of contact with authorities. "Silence before actions" refers to, for instance, rogue fishers who turn their radios off before entering restricted fishing zones.

The invention described herein includes a multi-graph modeling methodology in fusing various collection sources of a target system across spatial and temporal scales into a multi-graph representation. Additionally, the invention includes multi-layer information dynamics algorithms that analyze flows of a complex system (e.g., communication flows, vessel flows, fisheries flows in illegal fishing scenarios). For instance, a flow entropy measure quantifies flow complexity; a flow supra-Laplacian matrix captures inter-layer and intra-layer flow dependency; and a flow transfer entropy measure computes flow transfer dynamics on multi-graphs for activity and behavior detections.

The disclosed invention has multiple advantages over current prior art. For instance, the system described herein fuses information from multiple heterogeneous data sources (e.g., movement data in automatic identification system (AIS) track, communication data, and social media data) into multi-layer information dynamic networks, whereas prior art only considers information dynamics in a single layer. Additionally, the system according to embodiments of the present disclosure provides quantification of high-order information dependency (i.e., how one type of "information flows" influences another same (or different) type of "information flows") compared with primitive information dependency (i.e., how the states of one variable influences the states of another variable) as disclosed in prior art. Further, the invention described herein provides quantification of "flow complexity" where information transfer is normalized by the flow density ("speed" of flow), compared with the normalization of population density in spatial entropy, as described in prior art.

The system according to embodiments of the present disclosure addresses the need of "sense making" from various collection sources, in particular detecting emerging activities and behaviors from weak signals embedded in a complex system, to advance the understanding of flow complexity, dependency, and dynamics in a complex system (e.g., illegal fishing operations, terrorist activities and threats). Some advantages of the system described herein include, but are not limited to, providing early instability detection based on changes in flow entropy (complexity) of a target system; providing dependency identification based on the recovery of inter- and intra-layer links; and providing activity and behavior detection by inference on lead-lag of flow transfers. Each of these aspects will be described in further detail below.

(3.1) System and Methodology

Figure 3:
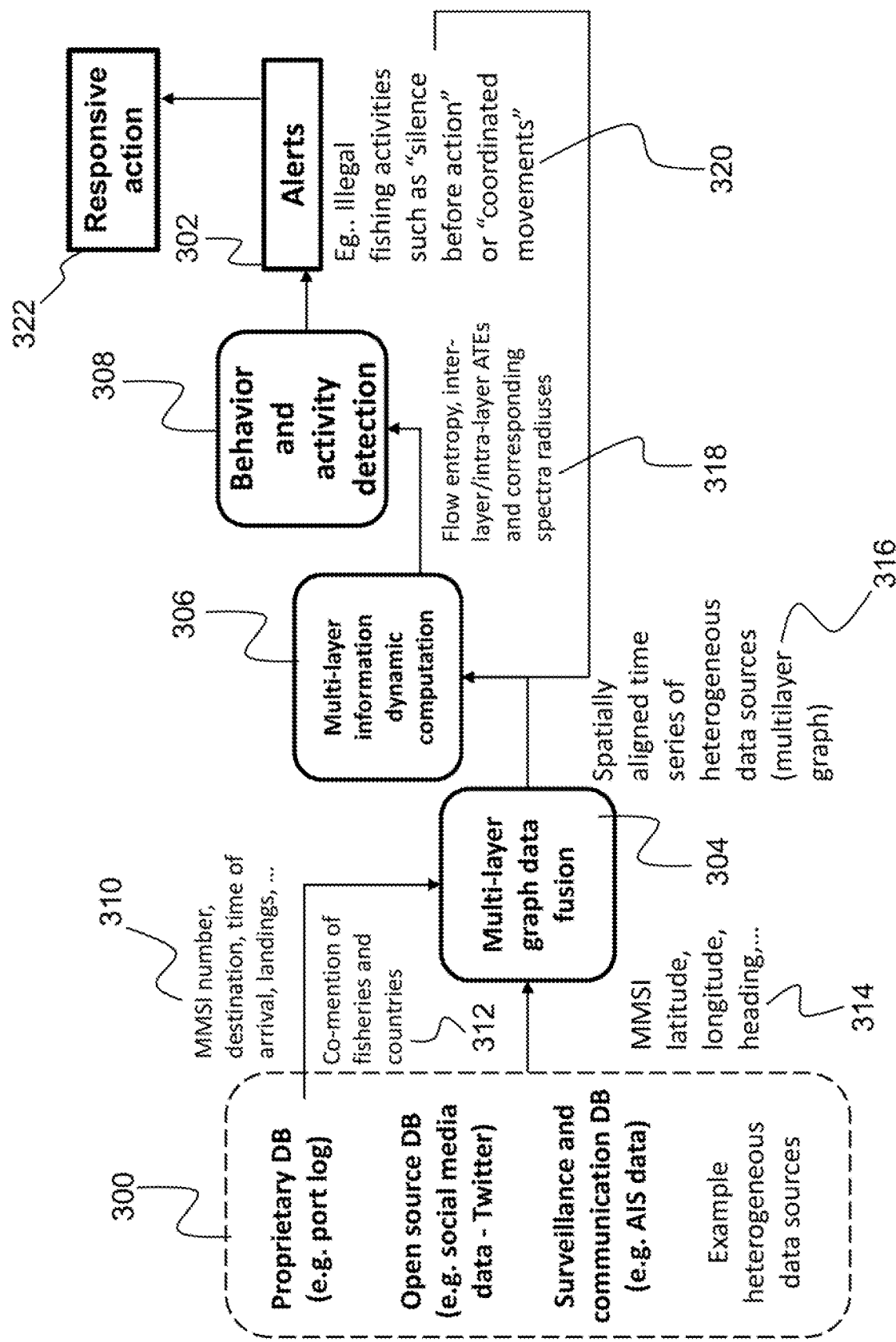
FIG. 3 is an illustration of the multi-layer information dynamics computational architecture according to some embodiments of the present disclosure.

FIG. 3 illustrates an overview of the computational framework of the multi-layer information dynamics according to embodiments of the present disclosure. The input to the system is extracted data from heterogeneous database (DB) sources 300 (e.g., proprietary DB sources, open source DB sources (social media), and surveillance and communication DB sources). The output of the system is a set of alerts 302 of emerging behaviors and activities, such as silence before actions and coordinated movements. An alert can be codified with event typology and relevant information, such as alert identification (ID), alert-time-stamp, event code, location, vessel, and probability. Additionally, an alert can be a message presented on a display to a user and/or an auditory alert. The system is comprised of a multi-layer graph fusion module 304, a multi-layer information dynamics computation module 306, and a behavior and activity detection module 308. Based on the alert 302, the system can initiate a responsive action, such as transmitting commands to an unmanned aerial vehicle (UAV) to physically maneuver or travel to the location to visually monitor the location and/or cause a satellite to direct one or more sensors toward the location and capture imagery of the location and transmit said imagery to a ground-based monitoring station.

Information gleaned from the heterogeneous DB sources 300 include, but are not limited to, maritime mobile service identity (MMSI) number, destination, time of arrival, and landings (element 310); co-mentions of fisheries and countries (element 312); and MMSI latitude, longitude, and heading (element 314). The output of the multi-layer graph fusion module 304 is spatially aligned time series of the heterogeneous data sources (i.e., multi-layer graph) (element 316). The output of the multi-layer information dynamics computation module 306 is flow entropy measures, inter-layer/intra-layer associative transfer entropies (ATEs), and corresponding spectra radiuses (element 318). The output of the behavior and activity detection module 308 is the set of alerts 302, non-limiting of examples of which include alerts of illegal fishing activities such as "silence before action" or "coordinated movements" (element 320). The details of each of the modules will be described in the following sections. Based on the alert 302, the system can initiate a responsive action 322, as described above.

(3.2) Multi-Layer Graph Data Fusion (Element 304)

The multi-layer graph data fusion module 304 starts with decomposing problem domains as multi-layer networks, where data sources, nodes, inter/intra-layer relations, and potential exploratory analyses are defined. As a non-limiting example, illegal fishing activities are modeled with multi-layer graphs (see FIG. 4) consisting of maritime activity networks, fisheries supply-chain networks, and social networks.

Figure 4:
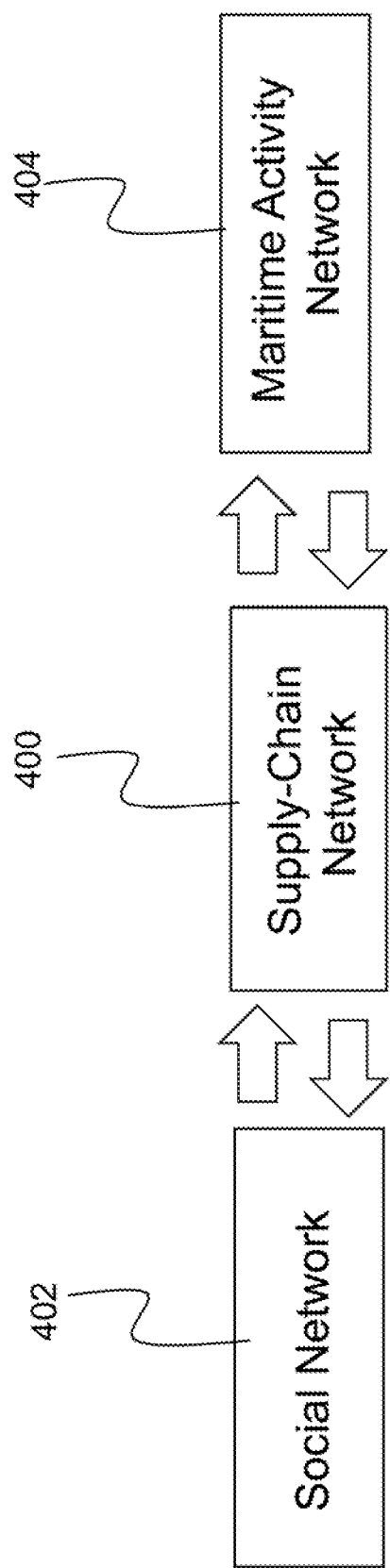
FIG. 4 is an illustration of multi-layer modeling of an illegal fishing capture supply-chain network, social network communication, and maritime activities according to some embodiments of the present disclosure.

FIG. 4 depicts a multi-layer network model according to embodiments of the present disclosure. The non-limiting example illustrated in FIG. 4 models illegal fishing capture supply-chain network and social network communication, in addition to maritime activities via conventional sensors, to derive economic and social indicators to enable early detection and prediction of illegal fishing activities (which may include behaviors). A supply-chain network layer 400 models logistics of fishing activities, such as vessels (e.g., fuel orders, fishing supplies) from port authorities' data, fishery products (e.g., processing, distribution, retails) from port factory and traffic data, and fishery product demand-supply from fishery import/export data. A social network layer 402 models social communications of fishing company employees, such as fishing crews, port workers, drivers, and market/restaurant customers in social media and open source data (e.g., Twitter, Tumblr, Yelp, LinkedIn, Forum).

A maritime activity network layer 404 models the movements and communication patterns of fishing fleets observed from heterogeneous sensor data sources, such as automatic identification system (AIS) data, ship-to-ship data, ship-to-shore data, and ship-to-central office communication data. The general idea of maritime activity network layers 404 is to consider vessel movement and communication patterns to perform exploratory data analysis for identifying and classifying illegal fishing activities conducted by individual and group vessels. FIG. 5 is a table showing initial network modeling, data sources, and potential exploratory analysis according to embodiments of the present disclosure. As depicted in FIG. 5, maritime activity network modeling can support exploratory data analysis of individual vessel and fleet trajectories to identify and classify illegal fishing activities.

Additionally, the purpose of supply-chain network layers 400 is to consider supply-demand of fisheries and the associated logistics such that exploratory data analysis can be performed to identify indicative signals for early detection and prediction for the trends of illegal fishing activities. FIG. 6 is a table depicting that supply-chain network modeling can support exploratory data analysis of vessel support logistics to identify early indicators of illegal fishing activities. Further, the purpose of the social network layer 402 is to consider social relations among agents (e.g., fishermen, crews, truck drivers, customers) that are involved in fishing and related fishery production and consumption activities, as shown in the table in FIG. 7.

Figure 8:
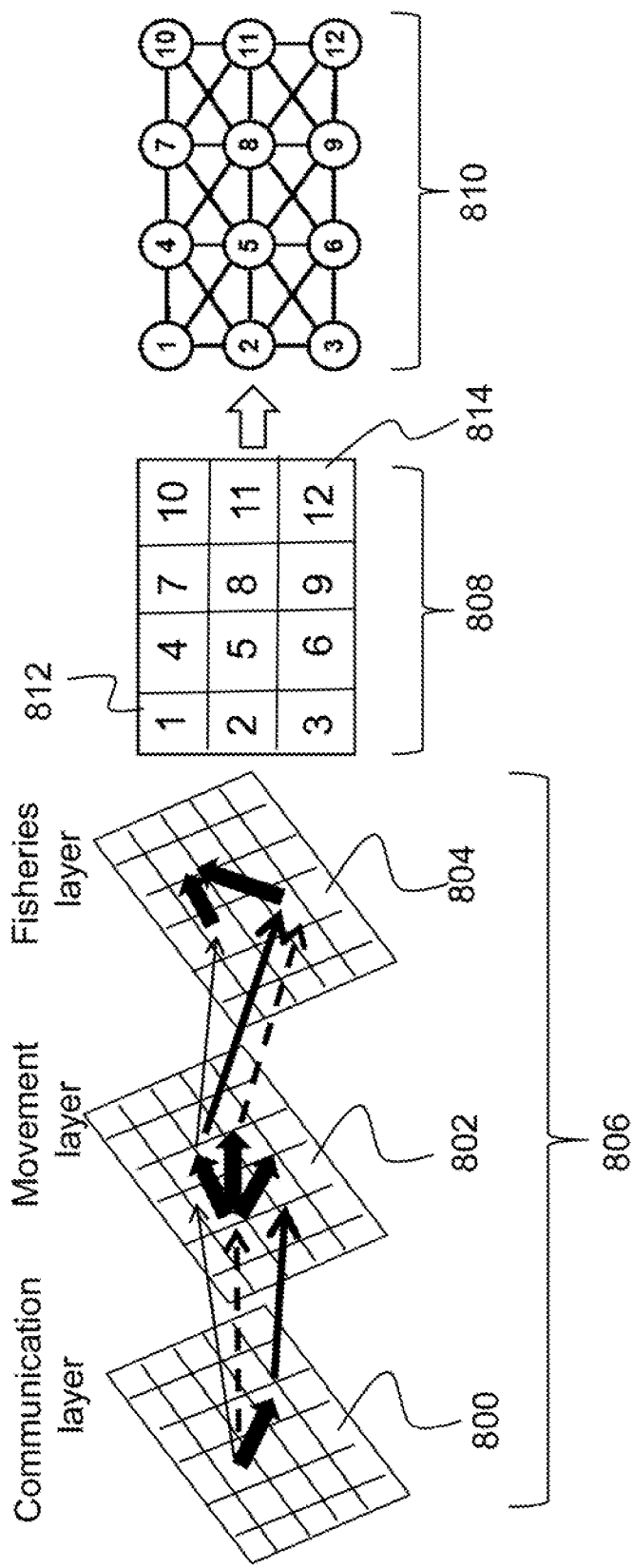
FIG. 8 is an illustration of three-layer network modeling of maritime activity capturing communication, vessels, and fishery flows transported among zones within each layer, and also coordinated flows between layers according to some embodiments of the present disclosure.

As illustrated in FIG. 8, maritime activities (element 404) are modeled with three network layers: vessel movements 800, communications 802, and fishery transports 804. It was observed that the fundamental characteristic of these three layers is flows. Flows are considered as the quantity of elements (e.g., the number of vessels, the frequency of communications, the number of fisheries) transported from one location to another for a given distance (e.g., miles a vessel travels, communication latencies, miles fisheries are transported). The multi-layer network according to embodiments of the present disclosure is defined where the nodes of each layer are the areas of entity locations (exclusive economic zones, ports), the intra-layer edges are flows (vessel flow, communication flow, and fishery flow) between zones within their respective layers, and the inter-layer edges are the dependency relationships of different types of flows (e.g., vessel flows depends on communication flows).

More formally, the N number of regions are denoted as $R_i$ for $i=1, 2, \ldots, N$. For instance, in the context of illegal fishing operations, the regions are spatial areas of longitude and latitude. Described herein is a complexity measure that describes the flows from region to region. $V_{R_i \to R_j}$ is defined as the number of vessels flowing from region $R_i$ to region $R_j$. If $i=j$, $V_{R_i \to R_i}$ describes the number of vessels staying in the region $R_i$. There will be up to $N(N-1)/2$ possible flows, but this number can be reduced by the moving speed of a vessel and the geography relations between zones. The probability of vessels moving from region $R_i$ to region $R_j$ is $$p_{ij} = \frac{V_{R_i \to R_j}}{\sum_{k=1}^{N} V_{R_i \to R_k}}.$$

The same formulation can be defined for communication and fishery flows.

The three-layer network modeling of maritime activity captures not only communication, vessels, and fishery flows transported among zones within each layer, but also coordinated flows between layers. Element 806 in FIG. 8 shows a concept illustration of the coordinated vessel movements and fishery transport originated by communication flows. Monitored regions are partitioned into 12 cells (element 808) and transformed as a graph (element 810) for capturing vessel movements given spatial constraints. For a vessel to move from cell/node 1 (element 812) to cell/node 12 (element 814), the vessel has to travel through one of the paths between node 1 and node 12; however, for vessel communication between regions, there are less rigid spatial constraints (e.g., node 1 can directly communicate with node 12).

The multi-layer data fusion module 304, therefore, amounts to resampling, interpolating, and aligning raw data from a heterogeneous database for corresponding modeled layers into spatially aligned time series for nodes defined in each network layer. For example, monitored regions are partitioned into small cells (nodes), where regions may have heterogeneous sizes and locations, but no overlaps. In addition, fishing vessel movements will adhere to spatial constraints (i.e., moving from one location to another via physically constrained paths (via neighboring cells), whereas communication is likely less rigid than spatial constraints.

(3.3) Multi-Layer Information Dynamic Computation (Element 306)

Described below are the main information-theoretic measures according to embodiments of the present disclosure: flow entropy (FIG. 9), flow transfer entropy (FIG. 10), and flow supra adjacency matrix (FIG. 11).

(3.3.1) Flow Entropy

First, the applicability of Shannon's entropy was examined for the flows according to the following:

$$H_i = \sum_{j=1}^{N} p_{ij} \log p_{ij},$$

which measures the complexity of the outward flow distributions from region $R_i$, where p denotes probability. This measure does not distinguish whether all the vessels stay in region $R_i$ or move to a single other region $R_j$, because $H_i=0$ for either case. To better capture the flow complexity, the flow distance from one region to another is taken into account, and $d_{ij}$ is defined as the distance between the centroids of $R_i$ and $R_j$. In analogy to the definition of spatial entropy, where the number of events is relative to spatial areas (spatial distribution), the flow entropy is defined, where the number of events is relative to flow distances (flow distribution).

The flow entropy originating from region $R_i$ is defined $$S_i = \sum_{j=1}^{N} p_{ij} \log p_{ij},$$

where $$\rho_{ij} = \frac{p_{ij}}{e^{-d_{ij}}}$$

is the probability 'speed'. d represents distance between regions i and j. As a non-limiting example, d could be defined as the centroid of region i to the centroid of region j (or other suitable definitions of distance between two spatial regions). The flow entropy is defined as $$S = \sum_{i=1}^{N} S_i = \sum_{i=1}^{N} \sum_{j=1}^{N} p_{ij} \log \rho_{ij}.$$

The flow entropy is 0 when all the vessels stay stationary and maximized when all the vessels travel out and go into different regions skewed by the flow distance. If all the vessels travel to a single region, it will still meet the desired property that the complexity is nonzero (or positive). In other words, the flow entropy according to embodiments of the present disclosure measures the complexity of flows in spatial systems by examining changes in flow density and their flow distances in the spatial regions, whereas the spatial entropy measures the complexity of spatial systems by examining changes in the number of events and their density in the spatial regions.

For a closed system, the overall flow entropy is balanced. In other words, the sum of out-flow entropy equals to the sum of in-flow entropy ($S^{out}=S^{in}$), yet each region can have different net-flow entropy ($S_i^\Delta = S_i^{in} - S_i^{out}$), where out-flow entropy is defined as $$S^{out} = \sum_{i=1}^{N} S_i^{out} = \sum_{i=1}^{N} \sum_{j=1}^{N} p_{ij} \log \rho_{ij}$$

and $$S^{in} = \sum_{i=1}^{N} S_i^{in} = \sum_{i=1}^{N} \sum_{j=1}^{N} p_{ij} \log \rho_{ij}.$$

It would be interesting to further explore the characteristics of flow entropy in dissipative systems.

Figure 9:
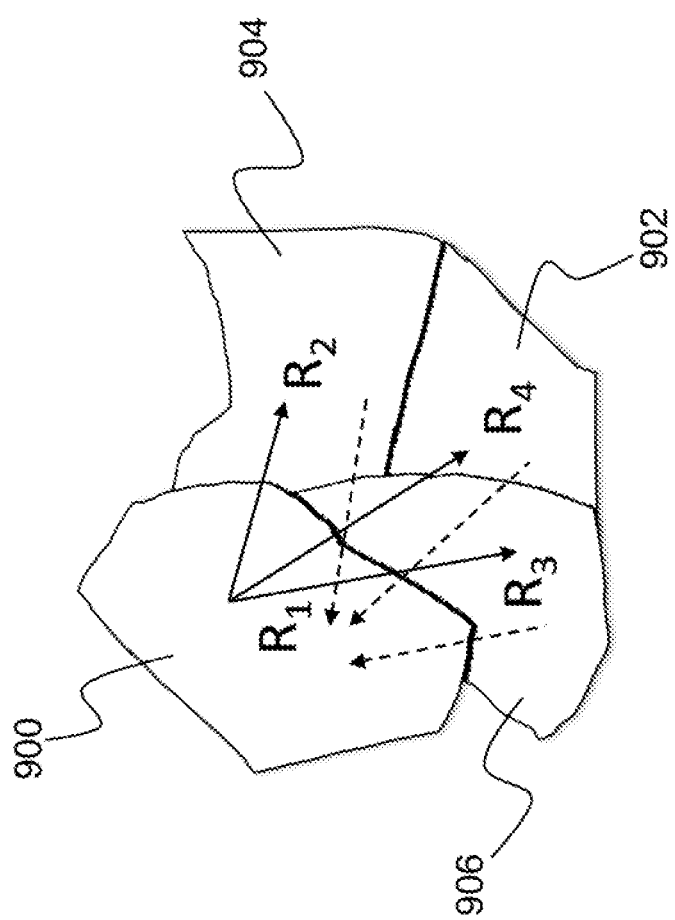
FIG. 9 is an illustration of flow entropy as a complexity measure defined to capture flow event density normalized by their flow distances according to some embodiments of the present disclosure.

FIG. 9 depicts flow entropy as a complexity measure defined to capture flow event density normalized by their flow distances. For example, the outward flow entropy from region $R_1$ (element 900) to the rest are depicted by solid arrows, where the flows toward $R_4$ (element 902) would require more efforts than $R_2$ (element 904) or $R_3$ (element 906) due to its flow distances. The inward flows are depicted by dashed arrows.

(3.3.2) Flow Transfer Entropy

The flows from region $R_i$ to region $R_j$ are denoted as $V_{R_i \to R_j}(t)$, $C_{R_i \to R_j}(t)$, and $F_{R_i \to R_j}(t)$ for vessels, communication, and fisheries, respectively. These are the edges in a multi-layer graph expressed as a supra-adjacency matrix, referred to as a supra-graph. The system described herein captures the dependency of these flows (edges) and their changes within and across different types of flows (e.g., communication, fishing vessels). The time series of intra-layer edges are observed for each layer (for example, the vessel flows during a fixed time interval changes over time) based on sensor data. For i=j, the time series will be density of vessels, communications, and fishery in each zone for the three layers: $V_{R_i \to R_i}(t)$, $C_{R_i \to R_i}$, and $F_{R_i \to R_i}(t)$, respectively. Next, inter-layer relations are constructed. Since the system aims to discover dependency of the flows from one layer to another, the inter-layer edges are between a pair of flows from different layers. The dependency is determined by computing associative transfer entropy (ATE): $ATE_{ij \to kl}$ ($C_{R_i \to R_j}(t)$, $V_{R_k \to R_l}(t)$) applied over the flows. The units are time series of edges/flows (e.g., ij or kl). A description of the computation of ATE can be found in U.S. patent application Ser. No. 13/904,945 entitled, "Detection and Identification of Directional Influences Using Dynamic Spectrum" (hereinafter referred to as the '945 application). The '945 application is hereby incorporated by reference as though fully set forth herein.

Figure 10:
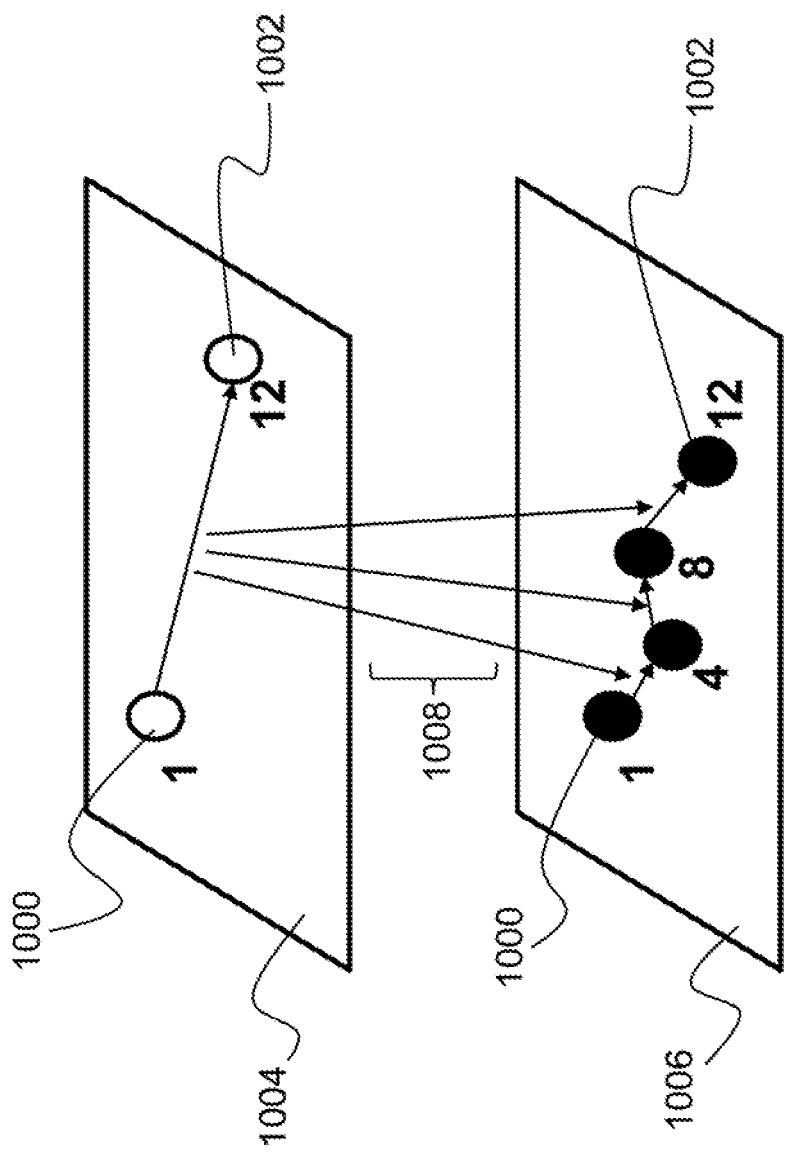
FIG. 10 is an illustration of the discovery of inter-layer dependency relations according to some embodiments of the present disclosure.

A schematic illustration of the discovery of inter-layer dependency relations is provided in FIG. 10. The communication flow between node 1 (element 1000) and node 2 (element 1002) in the upper panel 1004 influences the flows on the path of node 1→4→8→12 in the bottom panel (1006). Such flow dependency (represented by arrows 1008) between layers are inferred automatically by the ATE methods according to embodiments of the present disclosure.

(3.3.3) Flow Supra Adjacency Matrix

The flow supra-adjacency matrix of the maritime multi-layer networks according to embodiments of the present disclosure is denoted according to the following:

$$M(t) = \begin{pmatrix} M_{CC}(t) & M_{CV}(t) & M_{CF}(t) \\ M_{VC}(t) & M_{VV}(t) & M_{VF}(t) \\ M_{FC}(t) & M_{FV}(t) & M_{FF}(t) \end{pmatrix},$$

where $$M_{CC}(t) = \begin{pmatrix} C_{R_1 \to R_1}(t) & C_{R_1 \to R_2}(t) & \cdots & C_{R_1 \to R_N}(t) \\ \vdots & \ddots & & \vdots \\ C_{R_N \to R_1}(t) & \cdots & & C_{R_N \to R_N}(t) \end{pmatrix}.$$

$$M_{VV}(t) = \begin{pmatrix} V_{R_1 \to R_1}(t) & V_{R_1 \to R_2}(t) & \cdots & V_{R_1 \to R_N}(t) \\ \vdots & \ddots & & \vdots \\ V_{R_N \to R_1}(t) & \cdots & & V_{R_N \to R_N}(t) \end{pmatrix}$$

-continued $$M_{FF}(t) = \begin{pmatrix} F_{R_1 \to R_1}(t) & F_{R_1 \to R_2}(t) & \cdots & F_{R_1 \to R_N}(t) \\ \vdots & \ddots & & \vdots \\ F_{R_N \to R_1}(t) & \cdots & & F_{R_N \to R_N}(t) \end{pmatrix}$$

and $$M_{CV}(t) = (ATE_{ij \to kl}(C_{R_i \to R_j}(t), V_{R_k \to R_l}(t))_{ijkl}$$

and $M_{CF}(t)$, $M_{VC}(t)$, $M_{VF}(t)$, $M_{FC}(t)$, $M_{FV}(t)$ are defined in the similar form respectively.

The semantic meaning of ATE of inter-layer edges (FIG. 11) is defined as follows:

$$ATE_{\{C_{R_i \to R_j}\} \to \{V_{R_k \to R_l}\}}(t) \text{ of } M_{CV}(t)$$

is the temporal frequency of coordinated ship movements leading by communication flows between zones ($R_i \to R_j$). This quantity is considered as an inferred measure, which may reveal dependency patterns of coordinated ship movements triggered by communication flows, especially under conditions when communication contents are not directly observable due to encryption or other reasons.

$$ATE_{\{C_{R_i \to R_j}\} \to \{F_{R_k \to R_l}\}}(t) \text{ of } M_{CF}(t)$$

is the temporal frequency of coordinated fishery transports leading by communication flows between zones ($R_i \to R_j$). This quantity is considered as an inferred measure, which may is reveal dependency patterns of coordinated fishery transport triggered by communication flows.

$$ATE_{\{V_{R_i \to R_j}\} \to \{C_{R_k \to R_l}\}}(t) \text{ of } M_{VC}(t)$$

is the temporal frequency of coordinated communication flows leading by vessel movements between zones ($R_i \to R_j$). This is considered as an inferred measure, which may reveal dependency patterns of coordinated communication flows triggered by ship movements (e.g., communication of presences to avoid collisions).

$$ATE_{\{V_{R_i \to R_j}\} \to \{F_{R_k \to R_l}\}}(t) \text{ of } M_{VF}(t)$$

is the temporal frequency of coordinated fishery transports leading by vessel movements between zones ($R_i \to R_j$). This is considered as an inferred measure, which may reveal dependency patterns of coordinated fishery transport triggered by ship movements (e.g., fisheries transports from the satellite ships to the mother ship).

$$ATE_{\{F_{R_i \to R_j}\} \to \{C_{R_k \to R_l}\}}(t) \text{ of } M_{FC}(t)$$

is the temporal frequency of coordinated communication flows leading by fishery transport between zones ($R_i \to R_j$). This is considered as an inferred measure, which may reveal dependency patterns of coordinated communication flows triggered by fishery transport (movements). One can choose not to model this quantity, unless certain fishery transports do alter communication patterns (e.g., after illegal fisheries are transported to the mother ship, the communication patterns among satellite ships and mother have significantly changed). However, this is less likely the case.

$$ATE_{\{F_{R_i \to R_j}\} \to \{V_{R_k \to R_l}\}}(t) \text{ of } M_{FV}(t)$$

is the temporal frequency of coordinated vessel movements leading by fishery transport between zones ($R_i \to R_j$). This is considered as an inferred measure, which may reveal dependency patterns of coordinated vessel movements triggered by fishery transports. One may choose not to model this quantity. Additionally, one may choose not to model certain submatrices (e.g., $M_{FV}(t)$, $M_{FC}(t)$), if one considers such dependency relations are not informative or of no interest. Moreover, a sparse flow supra-adjacency matrix is expected due to spatial travel/transport constraints in zones.

To quantify subtle changes in a monitored system, the time series of spectral radius and the supremum of the absolute values of the eigenvalues of a matrix for the whole supra Laplacian matrix and for each submatrices in FIG. 11 were computed as an indicator for monitoring emerging instability and changes in dependency.

As illustrated in FIG. 11, the flow supra adjacency matrix according to embodiments of the present disclosure is defined to capture maritime activity dependency. Submatrices (intra-layer edges) on the diagonal are mostly observed, whereas the submatrices off-diagonal (inter-layer edges) are inferred by associative transfer entropy.

(3.4) Behavior and Activity Detection (element 308)

In this section, the behavior and activity detection method according to embodiments of the present disclosure is described using vessel movement and communication as an example.

Input: communication flow time series $C_{R_i \to R_j}(t)$ and vessel flow time series $V_{R_i \to R_i}(t)$.

Figure 12A:
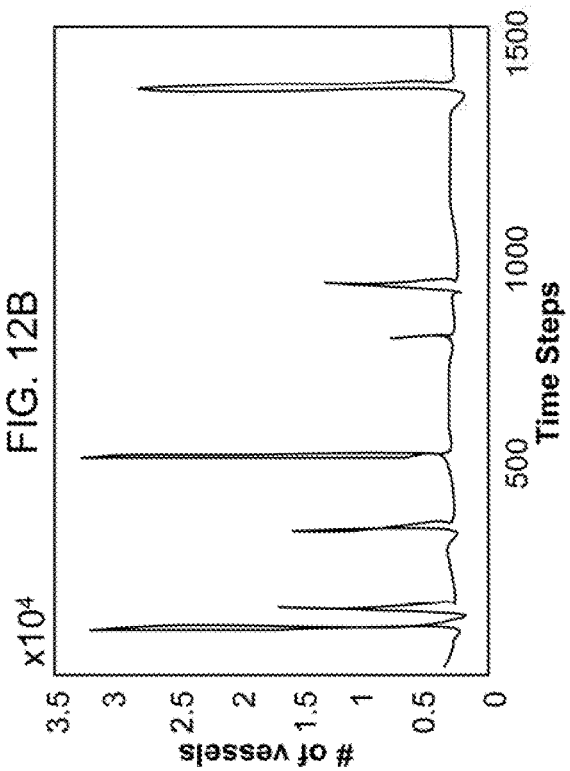
FIG. 12A is an illustration of time series of vessel flow from region i to region j according to some embodiments of the present disclosure.
Figure 12B:
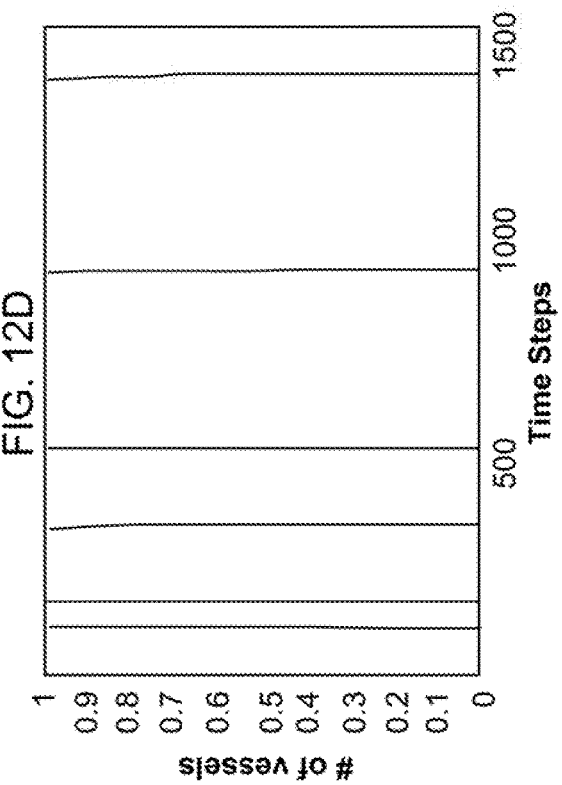
FIG. 12B is an illustration of time series of vessel flow from region i to region j according to some embodiments of the present disclosure.
Figure 12C:
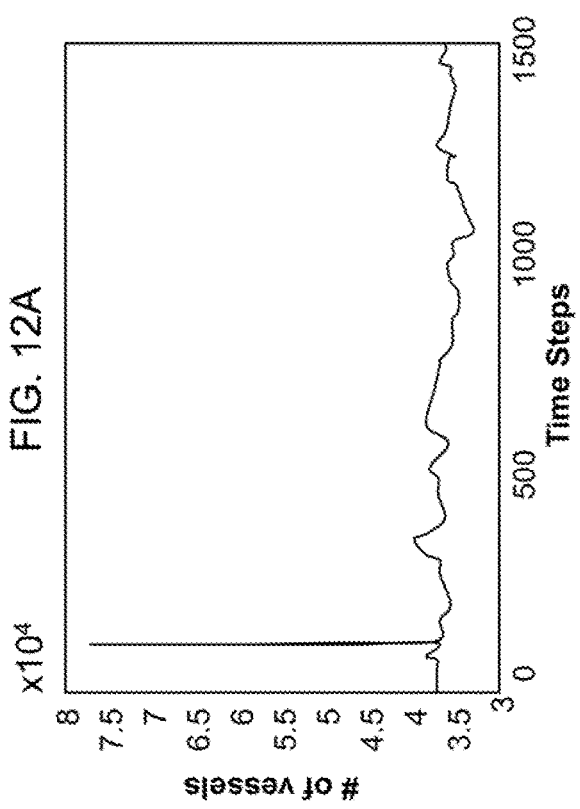
FIG. 12C is an illustration of a transformed spike time series of the time series of FIG. 12A according to some embodiments of the present disclosure.
Figure 12D:
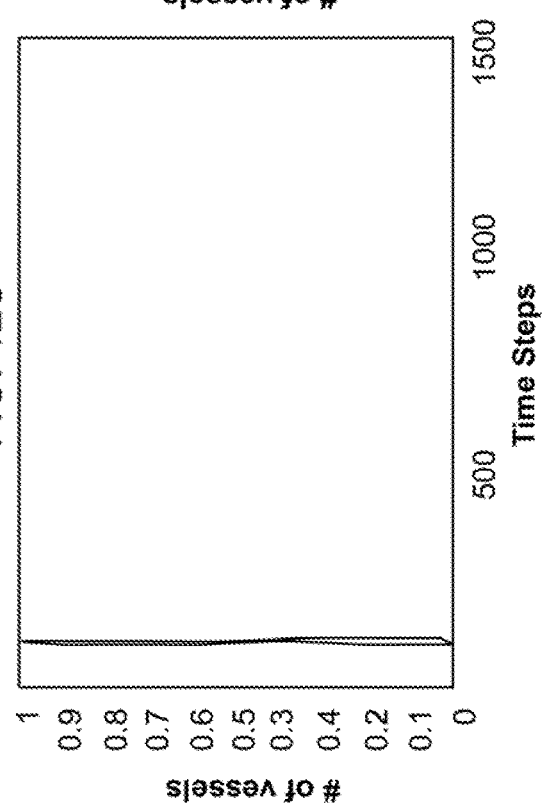
FIG. 12D is an illustration of a transformed spike time series of the time series of FIG. 12B according to some embodiments of the present disclosure.

Steps:
1) Signal symbolization: Transform the vessel flow time series into spike time series with values −1, 0, and 1, where −1 indicates a significant decrease in vessel flow compared to the previous time step, 0 indicates no effective changes, and +1 indicates a significant increase. A few examples are shown in FIGS. 12A-12D, where FIGS. 12A and 12B show the raw time series and FIGS. 12C and 12D show their corresponding transformed spike time series. The motivation to transform the time series is to obtain clearer signals because there are background vessel flow dynamics (the diffusion term) besides the vessel flow dynamics that is driven by the communication. The method according to embodiments of the present disclosure is a simple thresholding method of the flow ratio, where the ratio is the current vessel flow over the vessel flow at the previous time step. If the ratio is above 1/θ, then the flow exhibits a significant increase (rather than a purely background flow that doesn't deviate too much), symbolized with the value 1. If the ratio is below θ, then the flow exhibits a significant decrease. This is symbolized with the value −1. If the ratio is in between θ and 1/θ, then it is assigned to be 0. The θ value for example can be 0.9. Similar symbolization is executed for communication time series (i.e., transform communication time series into binary time series with 0's and 1's with a fixed threshold). This provides a simple symbolization method that transforms the communication time series into spikes time series for ATE calculation. Such a transformation step is not needed, if symbolized signals are provided as input.

2) Calculate ATE matrices: For each communication time series $C_{R_i \to R_j}(t)$ for i,j=1, . . . , N, the ATE from it to vessel flow time series $V_{R_k \to R_l}(t)$ is calculated for all k, l=1, . . . , N. This will require calculating $N^4$ ATEs, if one considers all possible combinations. This can be avoided by only considering the ij pairs of communication flows that are reoccurring (such as 10% of the times) and the kl pairs of vessel flows with $G_1(k,l) \neq 0$ (since there are no vessel flows between kl pairs with $G_1(k,l)=0$). In an experimental simulation scenario with chosen communication flows ($R_1 \to R_{12}$, $R_3 \to R_{12}$ and $R_5 \to R_{12}$), all three ATE matrices (from each of these communication flow time series to all vessel flow time series) are able to pick up the corresponding vessel flows. FIG. 13 shows the three ATE matrices with a simulation instance.

3) Detection: For each communication time series, the corresponding vessel flows were selected according to the ATE matrices with a simple thresholding method. The entries of an ATE matrix are sorted from high to low. Then, the ratios of the sorted entries (only the first 10% since only a few corresponding flows are needed) are taken to obtain the relative decrease. The maximum ratio provides the threshold to select corresponding vessel.

FIG. 13A is an illustration of a detected vessel flow path corresponding to the expected ground truth vessel flows given communication patterns. FIG. 13B is a plot illustrating inferred associative transfer entropy (ATE) between communication flow 1→12 and vessel flow i→j; FIG. 13C is a plot illustrating inferred ATE between communication flow 3→12 and vessel flow i→j; and FIG. 13D is a plot illustrating inferred ATE between communication flow 5→12 and vessel flow i→j.

(3.5) Simulation and Evaluation

The following section includes a description of the method according to embodiments of the present disclosure to evaluate the disclosed multi-layer information dynamics framework. Ground truth data of the vessel and communication flows were simulated using a semi-discrete parabolic process with added noises. During the evaluation, the performance (detection rate and false alarm rate) on simulated data was evaluated, assuming not knowing the ground truth scenarios.

(3.5.1) Semi-Discrete Parabolic Process on Multi-Layer Graph

Vessel flows that are driven by its own dynamics through diffusion and driven by communication flows are modeled through advection with the following equation:

$$\frac{\partial V}{\partial t} = \alpha \Delta_{G_{1,t}} V + \beta \nabla_{G_{2,t}} V + \gamma V + g. \quad \text{(Eq. 1)}$$

where on the left-hand side of the equation is the change of vessel density over a short time in a region. On the right-hand side of the equation, the first term models the vessel flow intra-layer dynamics with the graph Laplacian of graph structure $G_{1,t}$; the second term, advection, models the inter-layer influence of the vessel flows from the communication flows, where the graph derivative is informed by graph structure of the communication layer; and the third and fourth terms are reaction and source, respectively, and these terms were omitted for simulations.

(3.5.2) Simulation Method

Following are the simulation steps:

1) Generate vessel flow graph structure $G_{1,t}$. In experimental studies, small-world graphs with n=100 nodes and average degree equal to 6 were created. FIG. 14 shows such a graph structure. The structure can be changing over time. In the simulation, the structure was kept stationary $G_1$, since the physical constraints on how the regions connect to one another usually do not change.

2) Simulate communication patterns. These are the time series $C_{R_i \to R_j}(t)$ for i,j=1, . . . , N. In simulations, $R_1 \to R_{12}$, $R_3 \to R_{12}$, and $R_5 \to R_{12}$ were selected. For these time series $C_{R_i \to R_j}(t)$, 10% of the values are nonzero with magnitude equal to 1 (this could be generalized however) and the rest of the values are zero. The nonzeros are chosen (uniformly) random in time.

3) Simulate coordinated movements, for example:
   a. Communication $R_1 \to R_{12}$: vessel flows from $R_1 \to R_4$, $R_4 \to R_8$, and $R_8 \to R_{12}$.
   b. Communication $R_3 \to R_{12}$: vessel flows from $R_3 \to R_6$, $R_6 \to R_9$, and $R_9 \to R_{12}$.
   c. Communication $R_5 \to R_{12}$: vessel flows from $R_5 \to R_8$ and $R_8 \to R_{12}$.

4) Add noise into the simulation data. Add a random communication $C_{R_i \to R_j}(t)=e \in [0\ n]$ at each time t with a randomly chosen pair of i and j with i≠j. The variable n is the noise magnitude and e is chosen uniformly random from [0 n].

5) The graph structure $G_{2,t}$ (note that it's changing over time) is constructed according to the time series $C_{R_i \to R_j}(t)$ for i,j=1, . . . , N. Therefore, the communication noise together with the chosen communication flows ($R_1 \to R_{12}$, $R_3 \to R_{12}$, and $R_5 \to R_{12}$) drive the vessel flow $V_{R_i \to R_j}(t)$ through equation (Eq. 1).

6) To make it more difficult to infer the dependency of vessel flows and communications, the time up to d from the time of a spike is randomly delayed in the communication time series $C_{R_i \to R_j}(t)$ to the effective graph structure $G_{2,t}$ that drives the vessel flow. The delay time is randomly chosen from {1, 2, . . . , d} for each spike (nonzero) in $C_{R_i \to R_j}(t)$. Therefore, the effect of communication flows on vessel flows is not always an immediate effect nor a fixed delay of time.

(3.5.3) Evaluation Metrics

The following metrics are used to evaluate the detection method according to embodiments of the present disclosure:

1) Detection rate: The detection rate is the number of correct vessel flows over the number of the ground truth vessel flows.

2) False positive rate: The false positive rate is the number of the false positives over the sum of the false positives and true negatives. In this example, the number of true negatives were 600 (since there were 600 nonzeros entries in $G_1$) minus the number of ground truth vessel flows.

Figures 14A, 14B:
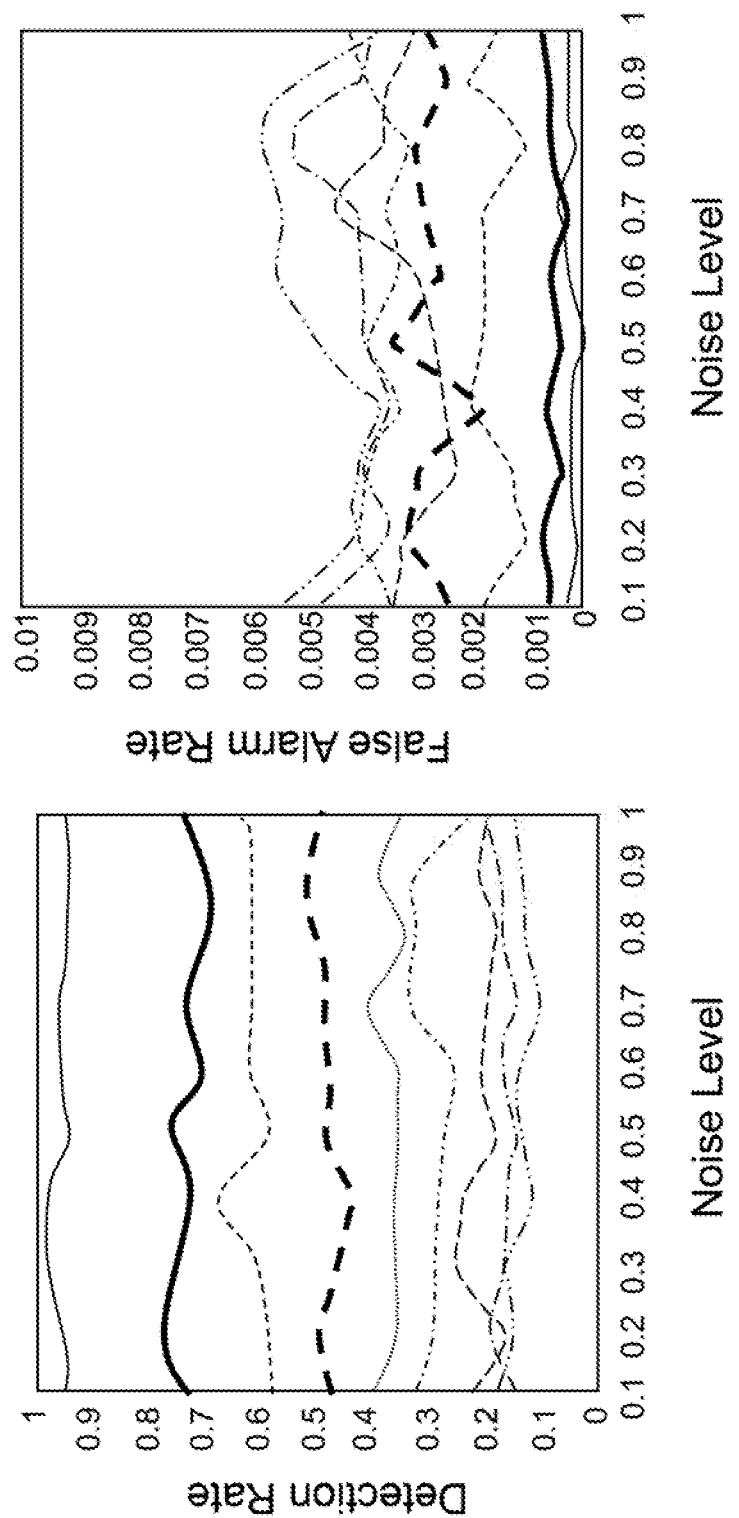
FIG. 14A is a plot illustrating detection rate results given observed noisy communication flows using the multi-layer information dynamics method according to some embodiments of the present disclosure.
FIG. 14B is a plot illustrating false alarm rates results given observed noisy communication flows using the multi-layer information dynamics method according to some embodiments of the present disclosure.

FIG. 14A is a plot illustrating detection rate results given observed noisy communication flows using the multi-layer information dynamics method. FIG. 14B is a plot illustrating false alarm rates results given observed noisy communication flows using the multi-layer information dynamics method. The multi-layer information dynamics method according to embodiments of the present disclosure shows robust detection results (high detection rate and low false alarm rates) for inferring the coordinated movements of vessel flows given observed noisy communication flows. These results show that the detection rate declines as the delay increases, but the noise magnitude can be at the same scale as the major communication flows. For instance, the detection rate is above 98% for delay=2. The false alarm rates are small in all cases and also are better when the delay becomes smaller.

(3.5.4) Results

1) Multiple scenarios were simulated with added noise, with different noise levels, and different communications to vessel flow delay times. The detection rate and the false alarm rate were obtained by averaging the detection rates and false alarm rates respective over 30 simulated instances per noise level.
2) In the results shown in FIGS. 14A and 14B, the noise level is the noise magnitude n (ranging from 0.1 to 1 with an increment of 0.1) that is described in Simulation Method step 4).
3) Each curve in the figure corresponds to a delay d (ranging from 1 to 10) that is described in Simulation Method step 5).
4) The time window for ATE calculation in the plots is 250 time steps, i.e. the detection is learned from 250 time steps.

(3.6) Experimental Studies

A demonstrator was built for experimental studies of the invention described herein. The demonstrator ingests various collection of data sources, simulates ship-to-shop communication data, computes and detects "silence before action" scenario and visualize the results.

(3.6.1) Data Sources & Preprocessing

The data sources used in the demonstrator include automatic identification system (AIS), port logs, and Twitter. The AIS data from the National Oceanic and Atmospheric Administration (NOAA) is a database of AIS broadcasts that each include a timestamp and a vessel's Maritime Mobile Service Identity (MMSI) call number, latitude, longitude, and heading. The database is processed by resampling and interpolating in time the broadcasts for each vessel to create a set of vessel position time series at a desired temporal frequency. The port log data is also from the NOAA and includes a history of voyages registered by vessels at various ports. Each voyage entry includes the vessel's MMSI number, intended destination, and estimated time of arrival. Only the voyages with destinations relevant to a Pacific crab fishing scenario of interest were filtered (e.g., destinations in Alaska, Russia, Korea, or Japan). The Twitter data comes from doing a cross-reference search on the Twitter database of countries and crab species (brown crab, Dungeness crab, king crab, snow crab, Tanner crab) according to embodiments of the present disclosure. The result is a set of tweets containing co-mentions of any pair of country/species. The tweets include the tweet text, date, and sometimes latitude and longitude coordinates. Data collection was focused on the Fall of 2013, because it includes the start of the short Alaskan crab fishing season and falls within the overlap of the AIS and Twitter data sources.

(3.6.2) Simulation

The scenario of interest for simulation was "silence before action." The simulation starts with real AIS data and simulates patterns of communication between the vessels. The initial communication pattern is based on vessels changing course because of a communication they received. An intuitive example might be a fishing vessel on its way to its usual fishing area that receives a communication informing it that the fish have been detected in a different area; the vessel then changes course to the new area based on that information. In the simulation of normal fishing operations, the probability of a vessel receiving a communication at a certain time is a function of the degree of change in movement direction by that vessel in the following hour time window. An area around the Aleutian Islands where crab fishing activity takes place is divided into a 25×25 grid, based on latitude and longitude. The movement layer is the number of vessels in each grid area at a given time. The communication layer is the number of communication messages received by vessels within each grid area at that time.

(3.6.3) Analysis

The associate transfer entropy between all pairs of time series within the movement layer, within the communication layer, and from the communication layer to the movement layer was computed. These are arranged into three 625× 625×time ATE matrices, for each of the movement-movement, communication-communication, and communication-movement layer pairs. The spectral radius is computed on each 625×625 matrix, resulting in a spectral radius time series. The plot of these spectral radius time series shows those related to the communication layer decreasing as the simulation transitions from normal to silent communication patterns, indicating that ATE spectral radius could be used as a metric to detect such a transition. The ATE matrices are also used to create a multi-layer graph. The 25×25 grid locations become nodes in the graph in two layers, one for movement and one for communication. A threshold is set on the ATE matrices, and edge is created between nodes whose ATE is above the threshold. The edges within and between the layers change over time with the simulation.

(3.6.4) Visualization

The display of the data sources and analysis can be integrated into one visualization. All the displays are synchronized in time so that they can be played through forwards and backwards to visualize the dynamics in the simulation and multi-layer graph. FIG. 15A illustrates automatic identification system (AIS) tracks 1500 on a map. FIG. 15B illustrates inferred multi-layer network with communication flows, movement flows, and their dependency changing over time. Communication flows are represented by dashed lines 1502 in the communication layer 1504. Movement flows are represented by solid lines 1506 in the movement layer 1508. The dependency of the flows changing over time is represented by bold lines 1510 between the communication layer 1504 and the movement layer 1508. FIG. 15C illustrates time series of Twitter country-fishery co-mentions (upper plot) and port log time series (lower plot), which can be used to look for correlations, and FIG. 15D illustrates the ATE spectral radius of inferred maritime activities according to some embodiments of the present disclosure, where each line in the plot represents combination vessel movements (M) and communication (C) with positive (p) or negative (n) ATE (i.e., MMp, MMn, MCp, MCn, CCp, CCn).

The disclosed invention can be deployed as embedded decision support modules in the cloud computing infrastructures or a stand-alone system for the application areas of complex systems, non-limiting examples of which include intelligence, surveillance and reconnaissance (ISR) for illegal fishing (as described herein) or other activities, crisis management, social unrests, and financial markets. The successful deployment of this technology is expected to result in detection and inference of system behaviors, activities, and dependency. Based on the detection and inference, the system can initiate a responsive action if desired. As a non-limiting example and as noted above, if illegal fishing is detected and/or inferred, the system can transmit instructions to cause a mobile platform (e.g., unmanned aerial vehicle, satellite, etc.) to maneuver sensors to be directed at the location and capture imagery of the location. For example, the system can cause a network enabled unmanned aerial vehicle (UAV) to travel (via the appropriate commands as understood by those skilled in the art) to the location of the illegal fishing and capture imagery of the location with a video camera. As another example, the system can transmit instructions to a satellite to direct one or more sensors to the location and capture imagery of said location from the earth's orbit. As can be appreciated by those skilled in the art, a number of other automated responsive actions can be initiated if a target activity is detected and/or inferred.

Furthermore, the system according to embodiments of the present disclosure addresses the significant need of "sense making" from large-scale, heterogeneous data sources for intelligence community and business analytics (Big Data and internet of things—IoT). The system is unique in the unusual recognition of "flows" as a common information unit across heterogeneous data sources, and the foreign concept of quantifying flow dependency within and across multi-layer information dynamics network. The demonstration of the system in the detection of "coordinated movements" and "silence before actions" for illegal fishing maritime activities, particularly, breaks the ground ("ocean") for better sense making.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while method steps have been recited in an order, the method steps may occur in any desired order and fall within the scope of the present invention.

What is claimed is:

1. A system for detecting activities and behaviors in a target system, the system comprising:
   one or more processors and a non-transitory computer-readable medium having executable instructions encoded thereon such that when executed, the one or more processors perform operations of:
      fusing raw data extracted from various heterogeneous sources of the target system across spatial and temporal scales into a multi-graph representation;
      quantifying flow complexity of the multi-graph representation using a flow entropy measure which captures flow event density normalized by flow distances;
      determining flow transfer dynamics on the multi-graph representation using a flow transfer entropy measure;
      identifying at least one of an economic and a social indicator of an activity of interest in the target system based on the flow entropy measure and the flow transfer entropy measure;
      detecting the activity of interest in the target system based on the at least one of the economic and the social indicator;
      outputting an alert of the detected activity of interest, wherein the alert is codified with at least one of an alert identification, an alert-time-stamp, and a location; and
      based on the alert, directing one or more sensors toward the activity of interest to capture imagery of the activity of interest.

2. The system as set forth in claim 1, wherein the one or more processors further perform an operation of determining values for a supra-Laplacian matrix as an indicator for monitoring emerging instability and changes in dependency in the target system.

3. The system as set forth in claim 1, wherein the one or more processors further perform an operation of initiating a responsive action in response to the prediction of the activity of interest in the target system.

4. The system as set forth in claim 1, wherein the set of multi-layer information dynamic measures comprises a flow supra-Laplacian matrix measure that captures inter-layer and intra-layer flow dependency.

5. The system as set forth in claim 1, wherein the one or more processors further perform operations of resampling, interpolating, and aligning raw data extracted from heterogeneous database sources into spatially aligned time series of the multi-graph representation.

6. The system as set forth in claim 1, wherein the one or more processors further performs an operation of modeling a fishing activity system with the multi-graph representation, wherein the multi-graph representation comprises a maritime activity network layer for modeling movement and communication patterns observed from heterogeneous sensor data sources, a supply-chain network layer for modeling logistics of fishing activities, and a social network layer for modeling social communication of employees related to fishing.

7. The system as set forth in claim 1, wherein the multi-graph representation comprises a plurality of layers, and wherein inter-layer and intra-layer dependencies of the multi-graph representation are determined using an associative transfer entropy (ATE) measure.

8. The system as set forth in claim 7, wherein the one or more processors further perform operations of:
   determining an ATE measure between all pairs of time series within and between layers of the multi-graph representation, resulting in a plurality of ATE measures;
   arranging the plurality of ATE measures into a plurality of ATE matrices;
   calculating a spectral radius on each ATE matrix, resulting in a spectral radius time series; and
   using the spectral radius time series to detect a transition in activity in the target system.

9. A computer implemented method for detecting activities and behaviors in a target system, the method comprising an act of:
   causing one or more processors to execute instructions encoded on a non-transitory computer-readable medium, such that upon execution, the one or more processors perform operations of:

fusing raw data extracted from various heterogeneous sources of the target system across spatial and temporal scales into a multi-graph representation;

quantifying flow complexity of the multi-graph representation using a flow entropy measure which captures flow event density normalized by flow distances;

determining flow transfer dynamics on the multi-graph representation using a flow transfer entropy measure;

identifying at least one of an economic and a social indicator of an activity of interest in the target system based on the flow entropy measure and the flow transfer entropy measure;

detecting the activity of interest in the target system based on the at least one of the economic and the social indicator;

outputting an alert of the detected activity of interest, wherein the alert is codified with at least one of an alert identification, an alert-time-stamp, and a location; and based on the alert, directing one or more sensors toward the activity of interest to capture imagery of the activity of interest.

10. The method as set forth in claim 9, wherein the one or more processors further perform an operation of determining values for a supra-Laplacian matrix as an indicator for monitoring emerging instability and changes in dependency in the target system.

11. The method as set forth in claim 9, wherein the one or more processors further perform an operation of initiating a responsive action in response to the prediction of the activity of interest in the target system.

12. The method as set forth in claim 9, wherein the set of multi-layer information dynamic measures comprises a flow supra-Laplacian matrix measure that captures inter-layer and intra-layer flow dependency.

13. The method as set forth in claim 9, wherein the one or more processors further perform operations of resampling, interpolating, and aligning raw data extracted from heterogeneous database sources into spatially aligned time series of the multi-graph representation.

14. The method as set forth in claim 9, wherein the one or more processors further performs an operation of modeling a fishing activity system with the multi-graph representation, wherein the multi-graph representation comprises a maritime activity network layer for modeling movement and communication patterns observed from heterogeneous sensor data sources, a supply-chain network layer for modeling logistics of fishing activities, and a social network layer for modeling social communication of employees related to fishing.

15. The method as set forth in claim 9, wherein the multi-graph representation comprises a plurality of layers, and wherein inter-layer and intra-layer dependencies of the multi-graph representation are determined using an associative transfer entropy (ATE) measure.

16. The method as set forth in claim 15, wherein the one or more processors further perform operations of:

determining an ATE measure between all pairs of time series within and between layers of the multi-graph representation, resulting in a plurality of ATE measures;

arranging the plurality of ATE measures into a plurality of ATE matrices;

calculating a spectral radius on each ATE matrix, resulting in a spectral radius time series; and using the spectral radius time series to detect a transition in behavior and/or activity in the target system.

17. A computer program product for detecting activities and behaviors in a target system, the computer program product comprising:

computer-readable instructions stored on a non-transitory computer-readable medium that are executable by a computer having one or more processors for causing the processor to perform operations of:

fusing raw data extracted from various heterogeneous sources of the target system across spatial and temporal scales into a multi-graph representation;

quantifying flow complexity of the multi-graph representation using a flow entropy measure which captures flow event density normalized by flow distances;

determining flow transfer dynamics on the multi-graph representation using a flow transfer entropy measure;

identifying at least one of an economic and a social indicator of an activity of interest in the target system based on the flow entropy measure and the flow transfer entropy measure;

detecting the activity of interest in the target system based on the at least one of the economic and the social indicator;

outputting an alert of the detected activity of interest, wherein the alert is codified with at least one of an alert identification, an alert-time-stamp, and a location; and based on the alert, directing one or more sensors toward the activity of interest to capture imagery of the activity of interest.

18. The computer program product as set forth in claim 17, further comprising instructions for causing the one or more processors to further perform an operation of determining values for a supra-Laplacian matrix as an indicator for monitoring emerging instability and changes in dependency in the target system.

19. The computer program product as set forth in claim 17, further comprising instructions for causing the one or more processors to further perform an operation of initiating a responsive action in response to the prediction of the activity of interest in the target system.

20. The computer program product as set forth in claim 17, wherein the set of multi-layer information dynamic measures comprises a flow supra-Laplacian matrix measure that captures inter-layer and intra-layer flow dependency.

21. The computer program product as set forth in claim 17, further comprising instructions for causing the one or more processors to further perform operations of resampling, interpolating, and aligning raw data extracted from heterogeneous database sources into spatially aligned time series of the multi-graph representation.

22. The computer program product as set forth in claim 17, further comprising instructions for causing the one or more processors to further perform an operation of modeling a fishing activity system with the multi-graph representation, wherein the multi-graph representation comprises a maritime activity network layer for modeling movement and communication patterns observed from heterogeneous sensor data sources, a supply-chain network layer for modeling logistics of fishing activities, and a social network layer for modeling social communication of employees related to fishing.

23. The computer program product as set forth in claim 17, wherein the multi-graph representation comprises a plurality of layers, and wherein inter-layer and intra-layer dependencies of the multi-graph representation are determined using an associative transfer entropy (ATE) measure.

24. The computer program product as set forth in claim 23, further comprising instructions for causing the one or more processors to further perform operations of:
- determining an ATE measure between all pairs of time series within and between layers of the multi-graph representation, resulting in a plurality of ATE measures;
- arranging the plurality of ATE measures into a plurality of ATE matrices; calculating a spectral radius on each ATE matrix, resulting in a spectral radius time series; and
- using the spectral radius time series to detect a transition in behavior and/or activity in the target system.

25. The system as set forth in claim 1, wherein the detected activity of interest comprises ship movement or the lack thereof.

26. The system as set forth in claim 9, wherein the detected activity of interest comprises ship movement or the lack thereof.

27. The system as set forth in claim 17, wherein the detected activity of interest comprises ship movement or the lack thereof.

* * * * *